US007442369B1

(12) United States Patent
Pena et al.

(10) Patent No.: US 7,442,369 B1
(45) Date of Patent: Oct. 28, 2008

(54) COMPOSITIONS OF MINOXIDIL

(75) Inventors: Lorraine Elisabeth Pena, Kalamazoo, MI (US); Maw-Sheng Wu, Mendham, NJ (US)

(73) Assignee: McNeil AB, Helsingborg (SE)

( * ) Notice: Subject to any disclaimer, the term of this patent is extended or adjusted under 35 U.S.C. 154(b) by 255 days.

(21) Appl. No.: 09/634,399

(22) Filed: Aug. 9, 2000

(51) Int. Cl.
*A61K 8/18* (2006.01)
*A61K 31/50* (2006.01)

(52) U.S. Cl. .................. 424/70.1; 424/78.02; 424/401; 424/487; 514/880; 514/247

(58) Field of Classification Search ................. 424/461, 424/484, 487, 70.1, 78.03, 78.08, 401; 514/57, 514/880, 944, 994, 247
See application file for complete search history.

(56) References Cited

U.S. PATENT DOCUMENTS

| | | | | |
|---|---|---|---|---|
| 3,461,461 | A | | 8/1969 | Anthony et al. |
| 4,139,619 | A | | 2/1979 | Chidsey, III |
| 4,478,853 | A | | 10/1984 | Chaussee |
| 4,596,812 | A | | 6/1986 | Chidsey, III et al. |
| 4,950,475 | A | * | 8/1990 | Vishnupad et al. ............. 424/83 |
| 5,059,606 | A | * | 10/1991 | Grollier et al. ........... 514/231.5 |
| 5,225,189 | A | | 7/1993 | Pena |
| 5,358,714 | A | * | 10/1994 | Green ......................... 424/400 |
| 5,505,934 | A | | 4/1996 | Meybeck et al. |
| 5,540,934 | A | * | 7/1996 | Touitou ...................... 424/450 |
| 5,620,980 | A | * | 4/1997 | Samour ...................... 514/256 |
| 5,654,337 | A | | 8/1997 | Roentsch et al. |
| 5,702,710 | A | * | 12/1997 | Charpentier et al. ......... 424/401 |
| 5,716,638 | A | * | 2/1998 | Touitou ...................... 424/450 |
| 5,776,480 | A | * | 7/1998 | Candau et al. .............. 424/401 |
| 5,976,515 | A | * | 11/1999 | Tsuji et al. ................. 424/70.1 |
| 6,001,812 | A | * | 12/1999 | Mahe .......................... 514/18 |
| 6,075,005 | A | * | 6/2000 | Lurie ............................ 514/2 |
| 6,106,848 | A | * | 8/2000 | Preuilh et al. ............... 424/401 |
| 6,124,362 | A | * | 9/2000 | Bradbury et al. ............. 514/569 |
| 6,171,604 | B1 | * | 1/2001 | Mousa ....................... 424/401 |
| 6,262,170 | B1 | * | 7/2001 | Kilgour et al. ............... 524/731 |
| 6,383,474 | B1 | * | 5/2002 | Soudant et al. ................ 424/59 |
| 6,468,551 | B1 | * | 10/2002 | Diec et al. ................... 424/401 |
| 2002/0013481 | A1 | * | 1/2002 | Schonrock et al. ........... 549/403 |
| 2002/0150600 | A1 | * | 10/2002 | Buchholz et al. ............ 424/401 |

FOREIGN PATENT DOCUMENTS

| | | |
|---|---|---|
| EP | 0 104 037 | 3/1984 |
| EP | 0 188 791 | 7/1986 |
| EP | 0 188 793 | 7/1986 |
| FR | 2 602 424 | 12/1988 |
| FR | 2 590 897 | 5/1997 |
| GB | 2 023 000 | 12/1979 |
| GB | 2 194 887 | 3/1985 |
| GB | 2 194 887 A | 3/1988 |
| GB | 2 194 888 | 3/1988 |
| JP | 61180709 | 8/1986 |
| JP | 63044512 | 2/1988 |
| JP | 63044513 | 2/1988 |
| JP | 63-145217 | 6/1988 |
| JP | 1503784 | 12/1989 |
| JP | 7048230 | 2/1995 |
| JP | 11092378 | 4/1999 |
| JP | 3502792 | 12/2003 |
| JP | 1211523 | 4/2008 |
| WO | WO88/01502 | 3/1988 |
| WO | WO 97/03676 | 2/1997 |
| WO | WO 97/03709 | 2/1997 |
| WO | WO 97/17077 | 5/1997 |
| WO | WO 98/33472 | 8/1998 |
| WO | WO 99/53923 | 10/1999 |
| WO | 00/07627 | 2/2000 |

OTHER PUBLICATIONS

Derwent Abstract of DE 19613698, published Jan. 23, 1997.*
Chiang, C., et al., "Bioavailability assesment of typical delivery systems: in vitro delivery of minoxidil from prototypical semi-solid formulations," *Intn. J. of Pharma.*, 1989, 49, 109-114.
Desal, D.D., et al., "Novel skin care formulations," *Cosmetics and Toiletries Manuf.*, 1997, 158-166.
Lieberman, H.A., et al. (Eds.), "Pharmaceutical Dosage Forms, Disperse systems," vol. 1, 2nd Ed, Refised and Expanded, 1989, 295-299.
Carbopol, "Product Guide," B.J. Goodrich, *Pharma. Bulletin 2*, Apr. 1995, 1-6.
Carbopol, "Nomenclature and Chemistry," B.F. Goodrich, *Pharma. Bulletin 3*, Apr. 1995, 1-17.
Carbopol, "Toxicology Studies," B.F. Goodrich, *Pharma. Bulletin 4*, Apr. 1995, 1-8.
Carbopol, "Emulsification Properties," B.F. Goodrich, *Pharma. Bulletin 13*, Apr. 1995.
Carbopol, "Formulating Topical Products," B.F. Goodrich, *Pharma. Bulletin 14*, Apr. 1995, 1-13.
"Surgical Lubricant Gel", PH-001T, B.F. Goodrich, *Pharma. Formulary*, May 1995, 28 pages.
Chiang, C.-M., et al., "Bioavailability assessment of topical delivery systems: in vitro delivery of minoxidil from prototypical semi-solid formulations," *International J. of Pharmaceutics*, 1989, 49, 109-114.

* cited by examiner

*Primary Examiner*—Sreeni Padmanabhan
*Assistant Examiner*—Kantamneni Shobha
(74) *Attorney, Agent, or Firm*—Woodcock Washburn LLP

(57) ABSTRACT

Novel compositions comprising minoxidil, a thickening agent, and a pharmaceutically acceptable solvent are presented. Also presented is a process for making a novel gel composition comprising minoxidil, and methods for using the novel compositions for treating and preventing hair loss in a region of a patient.

44 Claims, No Drawings

COMPOSITIONS OF MINOXIDIL

FIELD OF THE INVENTION

The present invention relates to novel compositions of minoxidil, methods for making the compositions, and methods for inducing and/or stimulating hair growth and/or reducing hair loss using the compositions.

BACKGROUND OF THE INVENTION

Minoxidil (i.e., 2,4-diamino-6-piperidinylpyrimidine-3-oxide) is the active ingredient of Loniten® and Rogaine®, which are marketed by Pharmacia & Upjohn as a treatment for hypertension, and as a treatment and preventative for androgenic alopecia (male and female pattern baldness), respectively. The preparation and antihypertensive use of minoxidil is described in U.S. Pat. No. 3,461,461. Methods and topical preparations for using the compound to grow hair and to treat male and female pattern baldness are described and claimed in U.S. Pat. Nos. 4,139,619 and 4,596,812.

Pharmaceutical compositions for topical application, such as Rogaine®, may take a variety of forms including, for example, solutions, gels, suspensions, and the like. Generally speaking, improved absorption may be achieved when the topical compositions are in the form of a solution or gel, i.e., where the active ingredient, for example, minoxidil, is dissolved in the carrier solution, in contrast to topical compositions which are in the form of suspensions, i.e., where the active ingredient is merely suspended in the composition.

Solutions of minoxidil typically contain water and one or more additional solvents. Topical solutions have not been entirely satisfactory for use in treating the scalp, however, as they tend not to remain in place long enough for satisfactory amounts of the drug to be absorbed. Formulations of minoxidil, such as jellies and ointments, have also been proposed. These compositions may not be pharmaceutically elegant, and also may not be suitable for use as treatments for stimulating the growth of hair, especially from a cosmetic point of view.

The use of polymeric thickening agents as part of the delivery vehicle for minoxidil, has also been described. GB 2 194 887, for example, describes a preparation containing a polymer, up to 20% solvent (i.e. propylene glycol), and up to 5% minoxidil. This application teaches that at least a part of the minoxidil may be in the form of micronized particles suspended in the delivery medium, however, rather than in solution. U.S. Pat. No. 5,225,189 also describes preparations containing a carbomeric polymer, and provides examples of single-phase gel preparations having up to 3% solubilized minoxidil therein.

Attempts to provide pharmaceutically appropriate thickened formulations containing higher concentrations of solubilized minoxidil are hampered, however, by various processing difficulties. For example, minoxidil is poorly soluble, and may precipitate out of solution by the addition of additional ingredients, such as thickening agents. Accordingly, high percentages of solvents, such as propylene glycol and alcohol, may be required. Frequently, however, these high solvent percentages may be incompatible with many pharmaceutical additives, such as thickening agents, and may generally result in a pharmaceutically inelegant product. Carbopol® 934P, for example, the carbomer polymer used in the examples of U.S. Pat. No. 5,225,189, in the presence of high percentages of solvent and inadequate amounts of water, affords a thick, doughy mass that may be unworkable with equipment commonly employed to manufacture pharmaceutical products.

There remains a need for new pharmaceutically elegant compositions of minoxidil which can be prepared using the equipment and techniques commonly used for the large scale, commercial production of topical pharmaceutical preparations. The present invention is directed to these, as well as other, important ends.

SUMMARY OF THE INVENTION

The present invention is directed, in part, to novel compositions of minoxidil. Specifically, in one embodiment, there is provided a composition comprising minoxidil, a non-carbomeric thickening agent, and a pharmaceutically acceptable solvent, wherein the minoxidil is substantially solubilized in said composition.

Another embodiment of the invention relates to a composition comprising greater than 3% minoxidil, a solvent-tolerant carbomer, and a pharmaceutically acceptable solvent, wherein said minoxidil is substantially solubilized in said composition.

Yet another embodiment of the invention relates to a composition comprising:
  from greater than about 3% to about 8% of minoxidil;
  from about 30% to about 80% of a polyol;
  from about 10% to about 50% of an alcohol;
  from about 0.01% to about 50% of a non-carbomeric polymer;
  from about 0% to about 3% of a neutralizing agent; and
  water (qs); wherein said minoxidil is substantially solubilized in said composition.

Still another embodiment of the invention relates to a non-gelled composition comprising minoxidil, a thickening agent, and a pharmaceutically acceptable solvent, wherein said minoxidil is substantially solubilized in said composition.

Another embodiment of the invention relates to a process for preparing a composition comprising:
  from greater than about 3% to about 8% of minoxidil;
  from about 30% to about 80% of a polyol;
  from about 10% to about 50% of an alcohol;
  from about 0.01% to about 50% of a non-carbomeric polymer;
  from about 0% to about 3% of a neutralizing agent; and
  water (qs); wherein said minoxidil is substantially solubilized in said composition, said process comprising:
  (a) providing a solution comprising said minoxidil, said polyol, a portion of said alcohol, and a substantial majority of said neutralizing agent;
  (b) providing a dispersion comprising said polymeric thickening agent, the remaining portion of said alcohol, any remainder of said neutralizing agent and said water; and
  (c) combining said solution and said dispersion to provide the gel composition.

Still another aspect of the invention relates to a process for preparing a non-gelled composition comprising minoxidil, a thickening agent, a pharmaceutically acceptable solvent, and water, wherein the minoxidil is substantially solubilized in the non-gelled composition, and wherein the process comprises combining together the minoxidil, thickening agent, pharmaceutically acceptable solvent and water to provide the composition.

Methods for treating and/or preventing hair loss in a region of a patient, wherein the methods comprise topically administering to the region compositions as described herein, are also provided by the present invention.

These and other aspects of the invention will become more apparent from the present disclosure and claims.

DETAILED DESCRIPTION OF THE INVENTION

The present invention is directed, in part, to novel compositions of minoxidil (i.e., 2,4-diamino-6-piperidinylpyrimidine-3-oxide) and their use in the treatment and/or prevention of hair loss. As noted above, the preparation and antihypertensive use of minoxidil is described in U.S. Pat. No. 3,461,461, and topical preparations and methods relating to the use of the compound to grow hair and to treat androgenic alopecia are described and claimed in U.S. Pat. Nos. 4,139,619 and 4,596,812. The disclosures of these three patents are hereby incorporated herein by reference, in their entireties.

The compositions of the present invention may take a variety of forms including, for example, gelled compositions and non-gelled compositions. The terms "gel" and "gelled composition", as used herein, refer to colloidal compositions which are preferably semisolid systems that may be composed of suspensions made up of small inorganic particles, or may comprise large organic molecules interpenetrated by a liquid. The term "non-gelled," as used herein, refers to compositions of the present invention which are not in the form of gels. Examples of non-gelled compositions include, for example, emulsions, thickened solutions, and the like. The term "thickened", as used herein, refers to compositions in which the viscosity has been enhanced to a viscosity greater than about that of water at ambient room temperature. The term "emulsion", as used herein, refers to a mixture of two or more liquids which may be in the form of a continuous phase and a disperse phase, for example. Exemplary emulsions may be in the form of creams or lotions, for example, and may include, for example, oil-in-water emulsions, water-in-oil emulsions, multiple emulsions and microemulsions. The term "suspension", as used herein, refers to a mixture or dispersion of finely divided particles floating in a liquid.

In preferred embodiments, the compositions of the present invention may be gels, with single-phase gels being more preferred. The term "single-phase gel", as used herein, refers to gels that may comprise organic macromolecules uniformly distributed throughout a liquid in such a manner that no apparent boundaries exist between the dispersed macromolecules and the liquid. Single-phase gels may be made from synthetic macromolecules (e.g., acrylic acid polymers) or from natural gums (e.g., Tragacanth).

The viscosity of the compositions of the present invention may vary and may depend, for example, on whether the compositions are gelled compositions or non-gelled compositions. In the case of gels, the compositions may have a viscosity at ambient room temperature which generally ranges from greater than about 4,000 centipoise to about 5 million centipoise, and all combinations and subcombinations of ranges and specific viscosities therein. More preferably, the gel compositions of the present invention may have a viscosity of from about 5,000 centipoise to about 50,000 centipoise, with viscosities of from about 6,000 centipoise to about 25,000 centipoise being even more preferred. In the case of non-gelled compositions, the compositions may have a viscosity at ambient room temperature which generally ranges from greater than about 6 centipoise to about 4,000 centipoise, and all combinations and subcombinations of ranges and specific viscosities therein. More preferably, the non-gelled compositions of the present invention may have a viscosity of from about 50 centipoise to about 3,000 centipoise, with viscosities of from about 100 centipoise to about 2,000 centipoise being even more preferred.

The concentration of the minoxidil in the present compositions may vary and may depend, for example, on the particular form of the composition, for example, whether the compositions are gelled compositions or non-gelled compositions. Broadly speaking, the minoxidil may be present in the present composition in an amount which ranges from greater than about 0.01% to about 8%, and all combinations and subcombinations of ranges and specific amounts therein. As used herein, the term "%" refers to weight %, unless otherwise indicated. In addition, the total % of components in the present compositions may not exceed 100%. In preferred embodiments, the minoxidil may be present in a concentration of greater than about 3%, with concentrations of greater than about 3% to about 8% being more preferred. In other preferred embodiments, concentrations of greater than 3% are preferred, with concentrations of from greater than 3% to about 8% being more preferred. In the case of certain preferred compositions, including certain gel compositions, the minoxidil may be present in a concentration of from about 4% to about 8%, about 5% to about 8%, about 6% to about 8% and about 7% to about 8%. In even more preferred embodiments, the minoxidil may be present in an amount of from about 4% to about 7%, or about 5% to about 6%, with concentrations of about 5% being particularly preferred.

The compositions of the present invention further preferably comprise a pharmaceutically acceptable solvent, and in preferred form, the minoxidil may be substantially solubilized therein. The term "substantially solubilized", as used herein, means that the minoxidil is dissolved in the compositions and is present at a concentration which is less than about its solubility limit in the present compositions. The term "pharmaceutically acceptable", as used herein, refers to materials which are generally not toxic or injurious to a patient when used in the compositions of the present invention, including when the compositions are applied topically according to methods described herein. The term "patient", as used herein, refers to animals, including mammals, preferably humans.

A wide variety of solvents may be used in the compositions of the present invention. Preferably, the solvent is a polar solvent. Preferred among these are polar, protic solvents. Preferably, the solvent is a hydroxy compound, i.e., a compound containing at least one hydroxy (OH) group. Preferred among the hydroxy compounds are alcohols (i.e., compounds containing one hydroxy group) or polyols (i.e., compounds containing two or more hydroxy groups) or mixtures of alcohols and/or polyols. Exemplary alcohols include, for example, ethanol, propanol and butanol. Reference herein to "ethanol" includes absolute alcohol, as well as "alcohol USP" and all denatured forms of 95% ethanol. As used herein, the term "propanol" refers to all isomeric forms, including n-propanol and isopropanol, and the term "butanol" refers to all isomeric forms, including, for example, n-butanol, iso-butanol and sec-butanol. Preferred among these alcohols are ethanol and propanol, with ethanol being more preferred. Exemplary polyols include, for example propylene glycol, dipropylene glycol, hexylene glycol, 1,3-butylene glycol, liquid polyethylene glycols, such as polyethylene glycol 200 (PEG-200) and polyethylene glycol 400 (PEG-400), and glycerol (the latter also referred to sometimes as glycerine). Preferred among these polyols is propylene glycol. In a particularly preferred embodiment, the solvent employed may be a mixture of an alcohol and a polyol.

The amount of solvent employed in the compositions of the present invention may vary and will depend, for example, on the particular solvent and thickening agent employed, the quantity of minoxidil employed, and the like. Preferably, the solvent may be employed in a quantity sufficient to assure that the minoxidil is solubilized in the present compositions. Preferably, the solvent may be employed in the present compositions in an amount ranging from about 1% to about 99%, and all combinations and subcombinations of ranges and specific amounts therein. More preferably, the solvent may be employed in an amount of at least about 20%. Even more preferably, the solvent may be employed in the present compositions in an amount of from about 20% to about 99%, with concentrations of from about 30 to about 80% being yet more preferred.

Preferably, the present compositions may comprise from about 30% to about 80% of a polyol and from about 10% to about 50% of an alcohol. More preferably, the present compositions may comprise from about 40% to about 70% of a polyol and from about 20% to about 30% of an alcohol. Even more preferably, the present compositions may comprise from about 50% to about 60% of a polyol and from about 25% to about 30% of an alcohol. Even more preferably, the present compositions may comprise about 53% of a polyol and about 26% of an alcohol.

Also in preferred form, the ratio of solvent to minoxidil in the present compositions is about 10:1. Ratios described herein are weight:weight ratios. Preferably, the ratio of solvent to minoxidil in the present compositions is about 12:1, with a ratio of about 15:1 being more preferred. Also in preferred form, the ratio of polyol to minoxidil in the present compositions is at least about 5:1. Preferably, the ratio of polyol to minoxidil in the present compositions is at least about 8:1, with a ratio of about 10:1 being more preferred. Further in preferred form, the ratio of alcohol to minoxidil in the present compositions is at least about 3:1. Preferably, the ratio of alcohol to minoxidil in the present compositions is at least about 4:1, with a ratio of about 5:1 being more preferred.

In accordance with preferred embodiments of the invention, the enhanced viscosities of the present compositions may be achieved through the use of thickening agents. The term "thickening agent", as used herein, refers to any of a variety of generally hydrophilic materials which, when incorporated in the present compositions, may act as viscosity modifying agents, emulsifying agents, gelling agents, suspending agents, and/or stabilizing agents. It is contemplated that the thickening agents may be capable of aiding in maintaining the stability of the compositions due to such properties. If desired, two or more thickening agents may be employed in the present compositions.

A wide variety of thickening agents are known to those skilled in the art and may be used in the practice of the present invention. In preferred embodiments, the thickening agent may be an organic thickening agent or an inorganic thickening agent, with organic thickening agents being more preferred. Preferred among the organic thickening agents are polymeric thickening agents. The term "polymer", as used herein, refers to molecules formed from the chemical union of two or more units. Accordingly, included within the term "polymer" are, for example, dimers, trimers and oligomers. The polymer may be synthetic, naturally-occurring or semi-synthetic. In preferred form, the term "polymer" refers to molecules which comprise 10 or more repeating units. Suitable polymeric thickening agents for use in the present compositions include, for example, starches, gums, pectin, casein, gelatin, phycocolloids and synthetic polymers. Exemplary of the foregoing materials are, for example, alginates and salts and derivatives thereof, including, for example, sodium alginate and propylene glycol alginate, acacia, carrageenan, guar gum, karaya gum, locust bean gum, tragacanth, xanthan gum, celluloses and salts and derivatives thereof including, for example, carboxymethylcellulose, carboxymethylcellulose sodium, carboxymethylcellulose calcium, ethylcellulose, hydroxyethylcellulose, methylcellulose, hydroxypropyl cellulose, hydroxypropyl methylcellulose, microcrystalline cellulose and powdered cellulose, hyaluronic acid and salts thereof such as, for example, sodium hyaluronate, gelatin and polydextrose.

Other polymeric thickening agents which may be employed include, for example, polymers of acrylic acid, such as crosslinked homopolymers of acrylic acid, crosslinked copolymers of acrylic acid, crosslinked interpolymers of acrylic acids, polyacrylic acid and salts thereof, acrylic/acrylate copolymers, dimethicone copolyols, polyacrylamide, ethylene/sodium acrylate copolymer, acrylamide/sodium acrylate copolymer, sodium acrylate/vinyl alcohol copolymer, sodium polymethacrylate, sodium polystyrene sulfonate, povidone and derivatives thereof, polyquaternium compounds, such as polyquaternium 10, polyvinyl alcohol, polyethylene oxide and poloxamers.

Any of the foregoing thickening agents may be employed in the compositions of the present invention. In certain preferred embodiments, the thickening agent may be a non-carbomeric thickening agent. The term "carbomer", as defined by the Cosmetics, Toiletry and Fragrance Association (CTFA), and as used herein, refers to synthetic, high molecular weight crosslinked homopolymers of acrylic acid. Examples of carbomers include, for example, Carbopols, such as Carbopol® 934P, Carbopol® 940, Carbopol® 980, Carbopol® 981 and Carbopol® Ultrez™ 10, commercially available from B.F. Goodrich (Cleveland, Ohio). The term "non-carbomeric", as used herein, refers to thickening agents that are not carbomers.

Certain carbomers are particularly useful in compositions which contain higher amounts of solvent, for example, protic solvents, such as alcohols and polyols, and lower amounts of water. Such carbomers are referred to herein as "solvent-tolerant carbomers," and include such carbomers as, for example, Carbopol® Ultrez™ 10 and Carbopol® 940, 941, 980 and 981 (all commercially available from B.F. Goodrich). In high solvent/low water compositions, such as those containing, for example, greater than about 50% solvent and/or less than about 25% water, these solvent-tolerant carbomers may be especially useful as viscosity modifying agents, i.e., they can be advantageously used to emulsify, gel, suspend, and/or stabilize the compositions. In contrast, other carbomers are not particularly adaptable to modifying the viscosities of high solvent/low water compositions, but are more advantageously employed in compositions containing lower amounts of solvent and/or higher amounts of water. Such carbomers which are not particularly useful in high solvent/low water compositions include, for example, Carbopol® 934P. Thus, for example, Carbopol® 934P is not a solvent-tolerant carbomer within the context of the present invention, and is not suitable for embodiments of the present invention that are characterized as being high solvent/low water compositions.

In the case of gel compositions, preferred thickening agents are copolymers of acrylic acid, with crosslinked copolymers of acrylic acid being more preferred. Particularly preferred among these thickening agents are acrylate/$C_{10-30}$ alkyl acrylate crosspolymers. Examples of acrylate/$C_{10-30}$ alkyl acrylate crosspolymers that may be suitable for use in the present compositions are Pemulen® polymeric emulsifiers, including Pemulen® TR 1 and Pemulen® TR 2, commercially available from B.F. Goodrich (Cleveland, Ohio).

In an alternate preferred embodiment of the present invention, the present compositions may comprise inorganic thickening agents. Suitable inorganic thickening agents include, for example, bentonite, magnesium aluminum silicate and colloidal silicon dioxide.

The amount of thickening agent employed in the present compositions may vary and depends, for example, on the particular polymer and solvent employed, the quantity of minoxidil, the desired viscosity of the final composition and the like. Generally speaking, the thickening agent may be employed in an amount to provide the compositions with a desired viscosity. Preferably, the thickening agent may be employed in an amount which ranges from about 0.01% to about 50%, and all combinations and subcombinations of ranges and specific amounts therein. More preferably, the thickening agent may be employed in an amount of from about 0.1% to about 3%, with from about 0.15% to about 0.6% being even more preferred.

The compositions of the present invention may further comprise one or more neutralizing agents, which may be used to adjust the pH of the compositions. The term "neutralizing agent", as used herein, refers to a material that may be used to modify the pH of the present compositions, for example, from an acidic pH to a more basic pH, or from a basic pH to a more acidic pH. Components of the present compositions, such as certain of the thickening agents, may be acidic, and may be preferably neutralized to achieve the desired thickening effect. Accordingly, the neutralizing agents are preferably those materials which may be used to modify the pH of the present compositions from an acidic pH to a more basic pH.

A wide variety of neutralizing agents are known to those skilled in the art and may be used in the practice of the present invention. Exemplary neutralizing agents include, for example, ammonium hydroxide, arginine, 2-amino-2-methyl-1-propanol (AMP-95® (Angus)), dimethanolamine, dibutanolamine, diisobutanolamine, tributanolamine, tri-isobutanolamine, tri-sec-butanolamine, tripropylamine, ethanolamine, diethanolamine, triethanolamine, PEG-15 cocamine, diisopropanolamine, methylethanolamine, diisopropylamine, dipropylenetriamine, tromethamine, isopropylamine ethylene diamine, triisopropanolamine, tetrahydroxypropyl ethylenediamine, trimethamine, 2-aminobutanol, aminoethyl propanediol, aminomethyl propanediol, aminomethyl propanol, sodium hydroxide, potassium hydroxide and mixtures thereof.

Preferably, the neutralizing agent is selected from 2-amino-2-methyl-1-propanol, diisopropanolamine, triisopropanolamine and tetrahydroxypropyl ethylenediamine, and mixtures thereof. More preferably, the neutralizing agent is 2-amino-2-methyl-1-propanol.

The amount of neutralizing agent employed in the compositions of the present invention may vary and will depend, for example, on the particular neutralizing and thickening agents employed, the quantity of thickening agent to be neutralized, the desired pH of the compositions, and the like. Preferably, the neutralizing agent may be employed in the present compositions in an amount which ranges from about 0% to about 5% (and all combinations and subcombinations of ranges and specific amounts therein), based on the total weight of the composition. More preferably, the neutralizing agent may be employed in the present compositions in an amount of from about 0% to about 3%. Even more preferably, the neutralizing agent may be employed in the present compositions in an amount of from about 0.03% to about 1%, with concentrations of from about 0.15% to about 0.6% being still more preferred.

The quantity of neutralizing agent used may also be expressed in terms of the ratio of thickening agent to neutralizing agent. Ratios described herein are weight:weight ratios. Preferably, the ratio of thickening agent to neutralizing agent is from about 10:1 to about 1:6, and all combinations and subcombinations of ranges and specific ratios therein. More preferably, the ratio of thickening agent to neutralizing agent is from about 2:1 to about 1:2, with a ratio of about 10:6 being even more preferred.

In addition to minoxidil, thickening agent and pharmaceutically acceptable solvent, the compositions of the present invention may further preferably comprise water. It has been found that desirable pharmaceutically elegant characteristics may be achieved by including water in the present compositions. The term "pharmaceutically elegant", as used herein, means that the compositions are preferably smooth, and not gritty or greasy to the touch. Preferably, water may be included in the present compositions in an amount of no greater than about 80%. More preferably, water may be employed in the present compositions in an amount which may range from about 0.1% to about 70%, and all combinations and subcombinations of ranges and specific amounts therein. Still more preferably, the water may be employed in the present compositions in an amount of from about 10% to about 25%, with amounts of from about 14% to about 16% being yet more preferred.

The compositions of the present invention may be topically administered to a region of a patient for the prevention or treatment of hair loss. Accordingly, as would be apparent to one of skill in the art, once armed with the teachings of the present disclosure, the compositions may optionally comprise additional pharmaceutically acceptable additives and ingredients such as, for example, hair conditioners, such as vitamin B5/panthenol, calcium pantothenate or other panthenol derivatives, colorants, fragrances, fragrance modifiers, other vitamins such as vitamin E, penetration modifiers, such as azone and DEET, surfactants, such as Cremophor® (BASF), cosmetic agents for the skin or scalp, such as fatty acids and fatty acid esters, herbal extracts, such as henna, other viscosity enhancing or thickening agents, oils, emulsifiers, wetting agents, sunscreens and anti-irritants.

A wide variety of methods may be used for preparing the compositions of the present invention. Broadly speaking, the compositions may be prepared by combining together the components of the compositions, as described herein, at a temperature and for a time sufficient to preferably provide a pharmaceutically elegant composition. The term "combining together", as used herein, means that all of the components of the compositions may be combined and mixed together at about the same time. For example, non-gelled compositions, including non-gelled compositions comprising minoxidil, a thickening agent, a pharmaceutically acceptable solvent, and water, may be prepared by combining together the minoxidil, thickening agent, pharmaceutically acceptable solvent and water to provide the non-gelled composition. In certain preferred embodiments, the term "combining together" means that the various components may be combined in one or more preferential sequences to provide the desired product.

In methods for forming non-gelled compositions, the water and thickening agent may preferably be combined together to produce a uniformly dispersed and hydrated mixture. To this can be added the solvent, and optionally, any neutralizing agent may be added. The minoxidil may then be added to the mixture, which may then be blended until the minoxidil is dissolved. Alternatively, the minoxidil may be first dissolved in the solvent, and then this mixture may be added to the mixture of the thickening agent and water.

Attempts to form pharmaceutically elegant polymeric gels of minoxidil by conventional means have in the past been hampered by processing difficulties, including (1) the poor solubility of minoxidil, (2) difficulties in obtaining effective and efficient dispersion of the thickening agent and maintenance of polymer solution; and (3) precipitation of the minoxidil. These problems are often exacerbated when using higher concentrations of minoxidil. For example, the use of higher amounts of minoxidil may require correspondingly higher amounts of solvent. However, the use of higher amounts of solvents results in the use of water in amounts that may be insufficient to provide a suitable dispersion of the thickening agent. On the other hand, the use of higher amounts of water may cause the minoxidil to precipitate.

In addition, conventional techniques for preparing gel formulations of a drug, which may involve, for example, the sequential mixing of a solvent, a thickening agent, a drug, and a neutralizing agent, have proven unsatisfactory in the case of gel formulations of minoxidil in that the combination of the components in the conventional manner results in the formation of a white precipitate. Analysis of this precipitate indicates the presence of both thickening agent and minoxidil.

It has been surprisingly and unexpectedly found, however, that a pharmaceutically elegant polymeric gel composition of the present invention, including gels comprising from greater than 3% to about 8% minoxidil, from about 30% to about 80% of a polyol; from about 10% to about 50% of an alcohol, from about 0.01% to about 3% of a non-carbomeric polymer, from about 0% to about 3% of a neutralizing agent, and a sufficient quantity of water can be conveniently and effectively produced by the methods disclosed herein. In preferred form, the method may comprise providing a solution comprising minoxidil, a pharmaceutically acceptable polyol, a portion of the alcohol and the neutralizing agent (step a). The method further preferably comprises providing a dispersion comprising the thickening agent, the remaining portion of the alcohol, and the water (step b). Both the solution and dispersion may be obtained, for example, by combining together the various components of the solution and dispersion, respectively. The solution and the dispersion may then be combined until a uniform gel composition is produced (step c).

Depending upon the thickening agent chosen, it may be possible to add all of the alcohol to the dispersion of step (b), rather than adding a portion of the alcohol to the minoxidil solution of step (a). Some thickening agents may not tolerate the high alcohol/low water environment, however, or will not produce a satisfactory or workable dispersion. Additionally, it has been found that the addition of some of the alcohol to the solution of step (a) may promote dissolution of the minoxidil in the polyol, and may, for example, avoid the necessity of heating the solution and permit step (a) to be performed at room temperature. Thus it is preferable that about 50% of the alcohol is used in the solution of step (a), and the remaining 50% is used in the dispersion of step (b).

A substantial majority of any neutralizing agent is preferably included in the solution of step (a), although a small percentage of the total amount of neutralizing agent may be included in the dispersion of step (b). As used herein, the term "substantial majority" refers to greater than about 80% of the total amount of the neutralizing agent, with greater than about 90% being preferred. Embodiments of the process wherein the neutralizing agent is substantially completely added to the solution of step (a) are even more preferred. As used herein, the term "substantially completely" means greater than about 99% of the total amount of neutralizing agent.

The compositions of the present invention may be advantageously employed to treat and/or prevent a region of hair loss or alopecia in a patient. Generally speaking, the methods may comprise topically administering to the region a composition as described herein. The life of a hair is subjected to a cycle, called the pilar cycle, during which the hair grows (anagen), transitions (catagen), and falls out (telogen), before being replaced by a new hair which appears in the same follicle and the cycle is repeated. This constant renewal process undergoes a natural change during ageing. The hair cycles become shorter, resulting in finer, shorter hairs. Hair loss results when this process is accelerated or disturbed, i.e. the growth phases become shorter, the passage of hair into the telogen phase is earlier and hairs fall out in larger numbers. Successive shortening growth cycles may result in increasingly fine and short hair, which is slowly converted into fluff. This phenomenon may lead to progressive hair thinning and may eventually lead to baldness.

Dermatologists recognize many different types of hair loss, the most common by far being androgenic alopecia (also known as "pattern baldness"), wherein humans begin losing scalp hair as they get older. While this type of hair loss is more common in males, it also occurs in women. This type of alopecia may be characterized by progressive thinning, as discussed above, or may be characterized by hair loss with little diffuse hair thinning, such as frontal hair loss, mid-anterior balding, bitemporal recession, and/or vertex balding. Alopecia greata, anagen hair loss, and diffuse alopecia, such as telogen effluvium are other presentations of hair loss, which may be distinguished from androgenic alopecia. These other forms or hair loss may also be treated with topical minoxidil.

The invention is further described in the following examples. All of these examples are actual examples. These examples are for illustrative purposes only, and are not to be construed as limiting the appended claims.

EXAMPLE I

A gel composition within the scope of the present invention and containing 5% minoxidil was prepared as follows:

Part I Solution

| | |
|---|---|
| Minoxidil USP | 50.7 mg |
| Propylene Glycol USP | 526 mg |
| Alcohol USP | 130 mg |
| AMP-95 ® (2-amino-2-methyl-1-propanol) | 1.5 mg |

Part II Dispersion

| | |
|---|---|
| Pemulen ® TR-1 NF | 2.5 mg |
| Purified Water USP | 153 mg |
| Alcohol USP | 136.3 mg |

Procedure

The alcohol and propylene glycol in Part I were mixed together, and the minoxidil was dissolved in the resulting solvent mixture. AMP-95® was added to the solution and mixed until dissolved. The alcohol and water in Part II were combined. The Pemulen® was gradually mixed into the alcohol/water mixture, until a uniform dispersion was produced. The Part I solution was then gradually added to the Part II dispersion with constant mixing, until a uniform gel developed. The resulting gel had a very nice appearance, with a smooth consistency, excellent clarity and a moderate viscosity.

EXAMPLE II

A minoxidil gel was prepared as described in Example I, except none of the alcohol was used in the Part I solution. It was necessary to heat the propylene glycol to dissolve the minoxidil, which remained in solution upon cooling to room temperature. The alcohol was then added to the solution, and the gel prepared, as in Example I. This example shows that mixing the alcohol and propylene glycol together prior to adding the minoxidil avoids the need for heating the solution to dissolve the minoxidil.

EXAMPLE III

A 5% minoxidil gel was prepared as follows:
Part I Solution

| | |
|---|---|
| Minoxidil USP | 22.14 mg |
| Propylene Glycol USP | 526 mg |

Part II Dispersion

| | |
|---|---|
| Pemulen ® TR-1 NF | 5 mg |
| Purified Water USP | 153 mg |
| Alcohol USP | 260.7 mg |

Part III Neutralizer

| | |
|---|---|
| AMP-95 ® (2-amino-2-methyl-1-propanol) | 5 mg |

Procedure

The propylene glycol and minoxidil were mixed together and heated to dissolve the minoxidil as in Example II. The alcohol and water from Part II were mixed and the minoxidil solution from Part I was added and mixed until uniform. The Pemulen® was gradually added to the minoxidil solution formed by combining Parts I and II. Upon initiating addition of the Pemulen® to the minoxidil solution, the mixture began forming a gel. Continued addition of Pemulen® resulted in a non-uniform mixture of non-dispersed small clumps of Pemulen® in the dry state and "fish eyes" (i.e. individual, partially hydrated gelatinous masses of Pemulen®). Continued mixing resolved the dry state clumps of Pemulen®, but the "fish eyes" remained. It was concluded that this would not be a suitable method of manufacture for the gel, so the manufacture was discontinued without addition of the AMP. This example demonstrates the need to prepare the minoxidil solution and Pemulen® dispersion separately.

EXAMPLE IV

A 5% minoxidil gel was prepared as follows:
Part I Solution

| | |
|---|---|
| Minoxidil USP | 175 g |
| Propylene Glycol USP | 1.75 kg |
| Alcohol USP | 770 g |
| DIPA | 17.5 g |

Part II Dispersion

| | |
|---|---|
| Carbopol ® 934P | 17.5 g |
| Purified Water USP | 770 g |

Procedure

The Part II dispersion was very thick and doughy, and was unacceptable for use in planetary mixers commonly used for gel manufacturing. A further attempt was made using differing ratios of water and alcohol in the Part II dispersion without improvement. In both cases, the combination of Part I with Part II resulted in precipitation of both the minoxidil and Carbopol® 934P. This example demonstrates that the gels of the present invention cannot be made by using Carbopol® 934P as the thickening agent.

EXAMPLE V

A gel composition containing 5% minoxidil was prepared as follows:
Part I Solution

| | |
|---|---|
| Minoxidil USP | 50.7 mg |
| Propylene Glycol USP | 473 mg |
| Alcohol USP | 130 mg |
| AMP-95 ® (2-amino-2-methyl-1-propanol) | 3 mg |

Part II Dispersion

| | |
|---|---|
| Pemulen ® TR-1 NF | 5 mg |
| Propylene Glycol USP | 52.6 mg |
| Purified Water USP | 153 mg |
| Alcohol USP | 130 mg |

Procedure

The Part I propylene glycol, alcohol and minoxidil were combined at room temperature and mixed. After a suitable mixing period, the minoxidil had failed to dissolve so the propylene glycol intended for Part II was added to Part I. The Part II dispersion was then prepared as described in Example I. The gel manufacture was completed as described in Example I. The resultant gel was comparable to that of Example I. This example demonstrates the importance of adding the entire quantity of propylene glycol to Part I.

EXAMPLE VI

A gel composition within the scope of the present invention and containing 5% minoxidil was prepared as follows:
Part I Solution

| | |
|---|---|
| Minoxidil USP | 50.7 mg |
| Propylene Glycol USP | 526 mg |
| Alcohol USP | 130 mg |
| Diisopropanolamine (DIPA) | 1.5 mg |

Part II Dispersion

| | |
|---|---|
| Carbopol ® 981 NF | 4.0 mg |
| Purified Water USP | 153 mg |
| Alcohol USP | 134.8 mg |

Procedure

The alcohol and propylene glycol in Part I were mixed together, and the minoxidil was dissolved in the resulting solvent mixture. Diisopropanolamine (DIPA) was added to the solution and mixed until dissolved. The alcohol and water in Part II were combined. The Carbopol® 981 NF was gradually mixed into the alcohol/water mixture, until a uniform dispersion was produced. The Part I solution was then gradually added to the Part II dispersion with constant mixing, until a uniform gel developed. The resulting gel had a very nice appearance, with a smooth consistency, excellent clarity and a moderate viscosity. This example demonstrates that the gel can be made with solvent-tolerant carbomers and alternate neutralizing agents.

EXAMPLE VII

A gel composition within the scope of the present invention and containing 5% minoxidil was prepared as follows:

Part I Solution

| | |
|---|---|
| Minoxidil USP | 50.7 mg |
| Propylene Glycol USP | 526 mg |
| Alcohol USP | 130 mg |
| AMP-95 ® (2-amino-2-methyl-1-propanol) | 1.5 mg |

Part II Dispersion

| | |
|---|---|
| Carbopol ® Ultrez ™ 10 | 2.5 mg |
| Purified Water USP | 153 mg |
| Alcohol USP | 136.3 mg |

Procedure

The alcohol and propylene glycol in Part I were mixed together, and the minoxidil was dissolved in the resulting solvent mixture. AMP-956) was added to the solution and mixed until dissolved. The alcohol and water in Part II were combined. The Ultrez™ 10 was gradually mixed into the alcohol/water mixture, until a uniform dispersion was produced. The Part I solution was then gradually added to the Part II dispersion with constant mixing, until a uniform gel developed. The resulting gel had a very nice appearance, with a smooth consistency, excellent clarity and a high viscosity. This example demonstrates that a variety of solvent-tolerant carbomers can be used to produce a broad range of viscosities.

EXAMPLE VIII

A gel composition within the scope of the present invention and containing 5% minoxidil was prepared as follows:

| | |
|---|---|
| Minoxidil USP | 50.7 mg |
| Propylene Glycol USP | 526 mg |
| Alcohol USP | 260.3 mg |
| Purified Water USP | 153 mg |
| Hydroxypropyl cellulose NF | 10 mg |

Procedure

The propylene glycol, alcohol, water and minoxidil were combined and mixed together until the minoxidil was dissolved. The hydroxypropyl cellulose was gradually mixed into the minoxidil solution until a uniform gel was produced. The resulting gel was clear and air-free with a moderate viscosity. This example demonstrates the use of non-carbomeric thickening agents and a suitable alternate method of manufacture.

The disclosures of each patent, patent application and publication cited or described in this document are hereby incorporated herein by reference, in their entirety.

Various modification of the invention, in addition to those described herein, will be apparent to those skilled in the art from the foregoing description. Such modifications are also intended to fall within the scope of the appended claims.

What is claimed is:

1. A composition in the form of a single-phase gel comprising from about 5% to about 8% minoxidil, a crosslinked copolymer of acrylic acid as a thickening agent, and a pharmaceutically acceptable solvent, wherein said minoxidil is present at a concentration which is less than its solubility limit in said composition.

2. A composition of claim 1 which comprises from about 5% to about 6% minoxidil.

3. A composition of claim 2 which comprises about 5% minoxidil.

4. A composition of claim 1, wherein said pharmaceutically acceptable solvent is selected from the group consisting of ethanol, propanol, butanol, propylene glycol, dipropylene glycol, hexylene glycol, 1,3-butylene glycol, PEG-200, PEG-400, glycerol and mixtures thereof.

5. A composition of claim 4, comprising a solvent selected from the group consisting of ethanol, propanol and butanol.

6. A composition of claim 5, comprising a solvent selected from the group consisting of ethanol and isopropanol.

7. A composition of claim 4, comprising a solvent selected from the group consisting of propylene glycol, dipropylene glycol, hexylene glycol, 1,3-butylene glycol, PEG-200, PEG-400, and glycerol.

8. A composition of claim 7, wherein said solvent comprises propylene glycol.

9. A composition of claim 4, wherein said solvent comprises a mixture comprising a first solvent selected from the group consisting of ethanol, propanol and butanol and a second solvent selected from the group consisting of propylene glycol, dipropylene glycol, hexylene glycol, 1,3-butylene glycol, PEG-200, PEG-400, and glycerol.

10. A composition of claim 9, wherein said solvent comprises a mixture of ethanol and propylene glycol.

11. A composition of claim 1, further comprising a neutralizing agent.

12. A composition of claim 11, wherein said neutralizing agent is selected from the group consisting of ammonium hydroxide, arginine, 2-amino-2-methyl-1-propanol, dimethanolamine, dibutanolamine, diisobutanolamine, tributanolamine, triisobutanolamine, tri-sec-butanolamine, tripropylamine, ethanolamine, diethanolamine, triethanolamine, PEG-15 cocamine, diisopropanolamine, methylethanolamine, diisopropylamine, dipropylenetriamine, tromethamine, isopropylamine ethylene diamine, triisopropanolamine, tetrahydroxypropyl ethylenediamine, trimethamine, 2-aminobutanol, aminoethyl propanediol, aminomethyl propanediol, aminomethyl propanol, sodium hydroxide, and potassium hydroxide.

13. A composition of claim 12, wherein said neutralizing agent is selected from the group consisting of 2-amino-2-methyl-1-propanol, diisopropanolamine, triisopropanolamine, and tetrahydroxypropyl ethylenediamine.

14. A composition of claim 13, wherein said neutralizing agent is 2-amino-2-methyl-1-propanol.

15. A composition of claim 1, wherein said solvent is present in said composition in an amount of at least about 20%.

16. A composition of claim 15 which comprises from about 20% to about 99% of said solvent.

17. A composition of claim 1, wherein said crosslinked copolymer of acrylic acid comprises an acrylate/$C_{10-30}$ alkyl acrylate crosspolymer.

18. A composition of claim 17 wherein said solvent is present in said composition in an amount of at least about 20%.

19. A composition in the form of a single-phase gel comprising:
from about 5% to about 8% of minoxidil;
from about 30% to about 80% of a first solvent selected from the group consisting of propylene glycol, dipropylene glycol, hexylene glycol, 1,3-butylene glycol, PEG-200, PEG-400, and glycerol;
from about 10% to about 50% a second solvent selected from the group consisting of ethanol, propanol and butanol;
from about 0.01% to about 50% of a crosslinked copolymer of acrylic acid;
from about 0% to about 3% of a neutralizing agent; and
water (qs);
wherein said minoxidil is present at a concentration which is less than its solubility limit in said composition.

20. A composition of claim 19, wherein said first solvent is propylene glycol.

21. A composition of claim 19, wherein said second solvent is selected from the group consisting of ethanol and isopropanol.

22. A composition of claim 19 wherein said crosslinked copolymer of acrylic acid comprises an acrylate/$C_{10-30}$ alkyl acrylate crosspolymer.

23. A composition of claim 19, wherein said neutralizing agent is selected from the group consisting of arginine, 2-amino-2-methyl-1-propanol, dimethanolamine, dibutanolamine, diisobutanolamine, tributanolamine, triisobutanolamine, tri-sec-butanolamine, tripropylamine, ethanolamine, diethanolamine, triethanolamine, PEG-15 cocamine, diisopropanolamine, methylethanolamine, diisopropylamine, dipropylenetriamine, tromethamine, isopropylamine ethylene diamine, triisopropanolamine, tetrahydroxypropyl ethylenediamine, trimethamine, 2-aminobutanol, aminoethyl propanediol, aminomethyl propanediol, and aminomethyl propanol.

24. A composition of claim 23, wherein said neutralizing agent is selected from the group consisting of 2-amino-2-methyl-1-propanol, diisopropanolamine, triisopropanolamine, and tetrahydroxypropyl ethylenediamine, and mixtures thereof.

25. A composition of claim 24, wherein said neutralizing agent is 2-amino-2-methyl-1-propanol.

26. A composition of claim 19, comprising:
from about 5% to about 7% of minoxidil;
from about 40% to about 70% of said first solvent;
from about 20% to about 30% of said second solvent;
from about 0.05% to about 3% of a crosslinked copolymer of acrylic acid; and
from about 0.03% to about 1% of a neutralizing agent.

27. A composition of claim 26, comprising:
from about 5% to about 6% of minoxidil;
from about 50% to about 60% of said first solvent; and
from about 25% to about 30% of said second solvent.

28. A composition of claim 26 comprising:
about 5% of minoxidil;
about 53% of said first solvent; and
about 26% of said second solvent;
from about 0.25% to about 1% of a crosslinked copolymer of acrylic acid; and
from about 0.15% to about 0.6% of a neutralizing agent.

29. A method comprising topically administering a composition according to claim 1 to a region of hair loss on a patient.

30. A method according to claim 29, wherein said hair loss is selected from the group consisting of androgenic alopecia, frontal hair loss, bitemporal recession, vertex balding, midanterior balding, alopecia greata, anagen hair loss, diffuse alopecia, and telogen effluvium.

31. A method comprising topically administering a composition according to claim 19 to a region of hair loss on a patient.

32. A method according to claim 31, wherein said hair loss is selected from the group consisting of androgenic alopecia, frontal hair loss, bitemporal recession, vertex balding, midanterior balding, alopecia greata, anagen hair loss, diffuse alopecia, and telogen effluvium.

33. A composition in the form of a single-phase gel consisting essentially of:
from about 5% to about 8% of minoxidil;
from about 30% to about 80% of a first solvent selected from the group consisting of propylene glycol, dipropylene glycol, hexylene glycol, 1,3-butylene glycol, PEG-200, PEG-400, and glycerol;
from about 10% to about 50% of a second solvent selected from the group consisting of ethanol, propanol and butanol;
from about 0.01% to about 50% of a crosslinked copolymer of acrylic acid;
from about 0% to about 3% of a neutralizing agent;
optionally, one or more pharmaceutically acceptable additives or ingredients selected from the group consisting of hair conditioners, panthenol, calcium pantothenate, colorants, fragrances, vitamin E, penetration modifiers, surfactants, cosmetic agents, fatty acids and fatty acid esters, herbal extracts, henna, wetting agents, sunscreens, and anti-irritants; and
water (qs);
wherein said minoxidil is present at a concentration which is less than its solubility limit in said composition.

34. A composition of claim 33, wherein said first solvent is propylene glycol.

35. A composition of claim 33, wherein said second solvent is selected from the group consisting of ethanol and isopropanol.

36. A composition of claim 33, wherein said crosslinked copolymer of acrylic acid is an acrylate/$C_{10-30}$ alkyl acrylate crosspolymer.

37. A composition of claim 33, wherein said neutralizing agent is selected from the group consisting of arginine, 2-amino-2-methyl-1-propanol, dimethanolamine, dibutanolamine, diisobutanolamine, tributanolamine, triisobutanolamine, tri-sec-butanolamine, tripropylamine, ethanolamine, diethanolamine, triethanolamine, PEG-15 cocamine, diisopropanolamine, methylethanolamine, diisopropylamine, dipropylenetriamine, tromethamine, isopropylamine ethylene diamine, triisopropanolamine, tetrahydroxypropyl ethylenediamine, trimethamine, 2-aminobutanol, aminoethyl propanediol, aminomethyl propanediol, and aminomethyl propanol.

38. A composition of claim 37, wherein said neutralizing agent is selected from the group consisting of 2-amino-2-methyl-1-propanol, diisopropanolamine, triisopropanolamine, and tetrahydroxypropyl ethylenediamine, and mixtures thereof.

39. A composition of claim 38, wherein said neutralizing agent is 2-amino-2-methyl-1-propanol.

40. A composition of claim 33, comprising:
from about 5% to about 7% of minoxidil;
from about 40% to about 70% of said first solvent;
from about 20% to about 30% of said second solvent; and
from about 0.05% to about 3% of a crosslinked copolymer of acrylic acid.

41. A composition of claim 40, comprising:
from about 5% to about 6% of minoxidil;
from about 50% to about 60% of said first solvent; and
from about 25% to about 30% of said second solvent.

42. A composition of claim 41 comprising:
about 5% of minoxidil;
about 53% of said first solvent;
about 26% of said second solvent; and
from about 0.25% to about 1% of a crosslinked copolymer of acrylic acid.

43. A method comprising topically administering a composition according to claim 33 to a region of hair loss on a patient.

44. A method according to claim 43, wherein said hair loss is selected from the group consisting of androgenic alopecia, frontal hair loss, bitemporal recession, vertex balding, mid-anterior balding, alopecia greata, anagen hair loss, diffuse alopecia, and telogen effluvium.

* * * * *